United States Patent [19]
Hansen

[11] Patent Number: 5,107,543
[45] Date of Patent: Apr. 28, 1992

[54] GOGGLE ENGAGING FACE MASK DEVICE AND METHOD

[76] Inventor: Gary M. Hansen, 12745 - 30th N.E., Seattle, Wash. 98125

[21] Appl. No.: 558,248

[22] Filed: Jul. 25, 1990

[51] Int. Cl.⁵ .................. A41D 13/00; A42B 1/00
[52] U.S. Cl. .............................. 2/9; 2/426; 2/427
[58] Field of Search ............ 2/9, 11, 15, 424, 425, 2/426, 427, 429, 430, 431

[56] References Cited

U.S. PATENT DOCUMENTS

| | | | |
|---|---|---|---|
| D. 220,376 | 4/1971 | Brown et al. | D2/232 |
| 1,123,376 | 1/1915 | Rextrew | 2/431 |
| 2,799,862 | 7/1957 | Rowe | 2/427 |
| 2,888,920 | 6/1959 | Mollering et al. | 128/141 |
| 3,103,667 | 9/1963 | Rogowski | 2/9 |
| 3,120,002 | 2/1964 | Blumenthal | 2/9 |
| 3,298,031 | 1/1967 | Morgan | 2/427 |
| 3,705,760 | 12/1972 | Langendorfer et al. | 351/44 |
| 3,710,393 | 1/1973 | Douglas | 2/430 |
| 3,943,574 | 3/1976 | Yamaguchi et al. | 2/9 |
| 4,250,577 | 2/1981 | Smith | 2/9 |
| 4,641,379 | 2/1987 | Martin | 2/9 |
| 4,653,124 | 3/1987 | McNeal et al. | 2/9 |
| 4,937,880 | 7/1990 | Beard | 2/9 |

FOREIGN PATENT DOCUMENTS

| | | | |
|---|---|---|---|
| 2607916 | 6/1988 | France | 2/426 |
| 657057 | 8/1986 | Switzerland | 2/424 |
| 817167 | 7/1959 | United Kingdom | 2/9 |

Primary Examiner—Werner H. Schroeder
Assistant Examiner—Michael A. Neas
Attorney, Agent, or Firm—Dean A. Craine

[57] ABSTRACT

Disclosed herein is a face mask device and method for protecting the face and eyes of a wearer and providing clear vision. The device includes a face mask structure and eye protecting device capable of engaging a conventional racing goggle worn over the device. The device comprises a face mask structure which covers all or a portion of the face area, a transparent, shatter-resistent eye protecting means which provides full vision, protects the eyes from injury, and engages the outer goggle place thereon. In the preferred embodiment, the eye protecting means comprises an eye piece with a round, forward protruding central region which slidable engages the inside surface of the outer goggle. The slidably engaging feature enables the outer goggle to be quickly and easily located and removed from the eye piece with one hand. A holding means is also provided which holds the device around the wearer's head. Optional air holes and slots may be manufactured on various areas on the face mask structure for ventilation and comfort. The method for maintaining clear vision includes repeatedly removing the most outer goggles from the goggle engaging face mask when vision is impaired, thereby exposing a lower clean goggle.

18 Claims, 3 Drawing Sheets

GOGGLE ENGAGING FACE MASK DEVICE AND METHOD

TECHNICAL FIELD

The present invention relates to face mask and eye protector devices. More particularly, the invention relates to combination face mask and eye protector devices capable of being used with an outer goggle.

BACKGROUND ART

Many activities and occupations, today, require an individual to use a face mask and goggles to protect their face and eyes. For some individuals, it is important that they have clear, adequate vision at all times while wearing the face mask and goggles.

Examples of individuals who need both face and eye protection and clear vision are those who participate in outdoor racing activities, such as jockeys or motorcyclists. It is known that while racing, mud, dirt and rain can impair the riders vision and that special precautions must be taken to maintain vision during the race. To provide clear vision during a race, jockeys often wear a plurality of racing goggles stacked one above another over their eyes. During the race, as mud, dirt, and rain is splattered on the outer most goggle, the jockey reaches up with one hand and quickly pulls the outer most goggle downward from the stack to expose the lower stacked goggle. By repeatedly removing the outer dirty goggle from the stack during the race in this fashion, the jockey is able to maintain clear vision throughout the race. These lightweight goggles, however, offer little or no protection for the eyes against hard, direct impacts.

Even though jockeys are often kicked by horses or hit with mud, dirt, and rain in face while racing, they generally do not wear face masks for several reasons. First, conventional face masks are uncomfortable to wear and generally impair their vision while racing. Second, even if vision were adequate with conventional face masks, they are not adequately designed to hold or to align an outer goggle over the eyes during use. Third, conventional face masks do not allow an outer goggle to be quickly and easily removed from the eyes with one hand when vision through the outer goggle is impaired, and do not provide a means for holding a plurality of stacked outer goggles over the eyes in the manner used by jockeys.

A face mask device, then, that is comfortable to wear, that protects the face and eyes, and that holds and allows the quick and easy exchange of outer goggles in the manner described above, would be highly desirable.

DISCLOSURE OF INVENTION

It should be understood that even though the invention disclosed herein is described in the context of jockeys, it may be used and applied in other fields.

It is an object of the present invention to provide a comfortable, lightweight, face mask device that will protect both the face and eyes of a wearer.

It is another object of the invention to provide a face mask device that while worn, causes little or no visual impairment to the wearer.

It is a further object of the invention to provide a face mask device that can securely hold an outer goggle placed over the face mask device.

It is a still further object of the invention to provide a face mask device that allows the outer most goggle on a stack of goggles placed over the face mask device to be easily and quickly exchanged with one hand so that clear vision may be maintained during a particular activity.

These and other objects of the invention which will become apparent from the goggle engaging face mask device disclosed herein, comprising a face mask structure, an eye protecting means, and a holding means. For maximum protection against hard, direct impacts to the face, the face mask structure is made of molded lightweight, shatter-proof material such as acrylic plastic or fiberglass. For individuals who need less protection, the face mask structure is made of flexible material, such as nylon or cotton. Generally, the face mask structure is manufactured to conform to the general features of the human face. While capable of being manufactured in any size and shape, in the embodiments disclosed herein, the face mask structure is spherical in cross-section and extends downward to protect all or a substantial portion of the wearer's face. Optional nose holes, a mouth opening and ventilation air holes and slots are also provided.

An eye protecting means protects the wearer's eyes and provides wide clear vision while the face mask device is worn. The eye protecting means is attached near and extends substantially across the eye region of the face mask structure. In the preferred embodiment, the eye protection means comprises a forward projecting, eye piece made of shatter-resistant transparent material. The eye piece is also spherical in cross-section similar to the face mask structure with a round, forward projecting central region. The round, forward projecting central region is complimentary in shape to the inside surface of an outer goggle. This enables the central region of the eye piece to be slidingly engaged by the outer goggle so that the outer goggle may be quickly and easily attached and aligned on the eye piece and, when desired, quickly and easily removed from the eye piece with one hand. Also, the forward projecting feature of the eye piece also allows additional goggles to be stacked above the first outer goggle without dislodging it from the eye piece. The central region of the eye piece may be manufactured in other shapes and configurations so that other outer goggle designs may slidingly engage the eye piece.

Various types of holding means, such as strap structures, are attached to the one or more lateral edges of the face mask structure to securely hold it in place against the wearer's face.

Also disclosed herein is a method of maintaining clear vision using the goggle engaging face mask device disclosed herein and a plurality of outer goggles stacked above the eye protecting means.

BEST MODE FOR CARRYING OUT THE INVENTION

Figure 1:
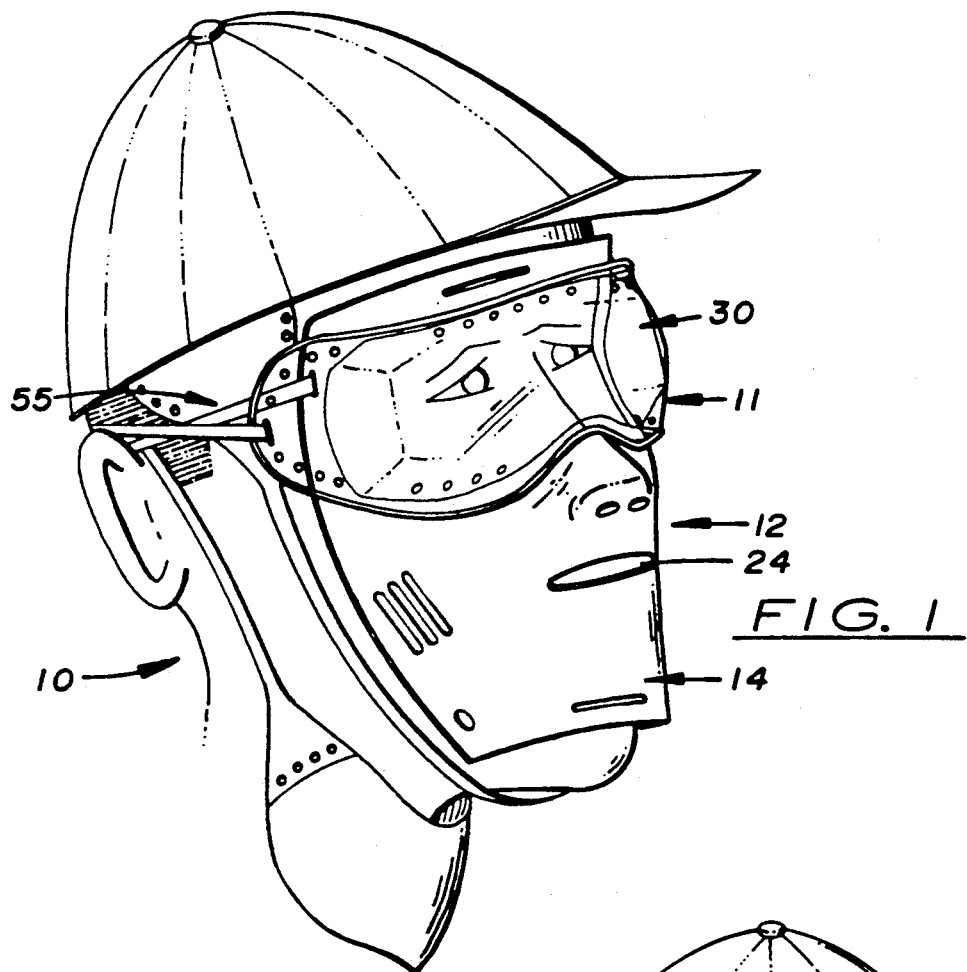
FIG. 1 is a perspective view showing the face mask device attached to a wearer with a conventional goggle placed over the eye protecting means.

FIG. 1 shows a face mask device 12 worn by a wearer 10 used to protect his face and eyes during an activity. The face mask device 12 comprises a face mask structure 14 designed to protect the wearer's face and an eye protection means shown in the preferred embodiment as a transparent eye piece 30 which protects the wearer's eyes. In addition to protecting the eyes, the eye protection means also acts to engage and hold an outer goggle 11 on the face mask device 12 during use. A holding means, shown in the preferred embodiment as a strap structure 55, holds the device 12 on the wearer's face.

Figure 2:
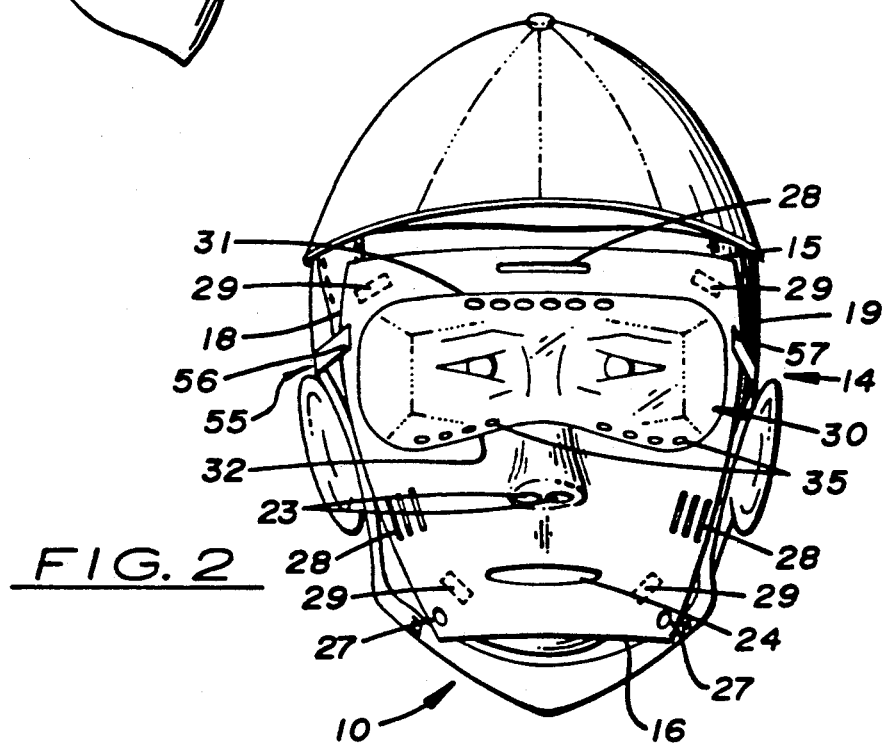
FIG. 2 is a plan view of an embodiment of the face mask device.

As shown in FIG. 2, the face mask structure 14 is manufactured to substantially conform in shape to a wearer's face. The face mask structure 14 may be manufactured to cover all or a portion of the face. The face mask structure 14 includes an upper edge 15 which extends horizontally across the forehead area, a lower edge 16 which extends horizontally across the mouth or lower jaw area, a first lateral edge 18 located on one side of the face mask structure 14, and a second lateral edge 19 located on the opposite side of the face mask structure 14. Optional nasal holes 23 and a mouth hole 24 may be manufactured centrally on the face mask structure 14 to facilitate breathing. Also, optional ventilation holes and slots 27 and 28, respectively, may be manufactured on the forehead, chin, and temporal regions for comfort. In the preferred embodiment, face mask structure 14 is made of lightweight shatter-resistent plastic or fiberglass material for maximum protection against direct impacts to the face. For special applications, where direct impacts to the face are unlikely, the face mask structure 14 may be made out of flexible material, such as nylon or cotton. Optional comfort pads 29 may be attached to the inside surface of the face mask structure 14 at various locations for additional comfort.

Figure 4:
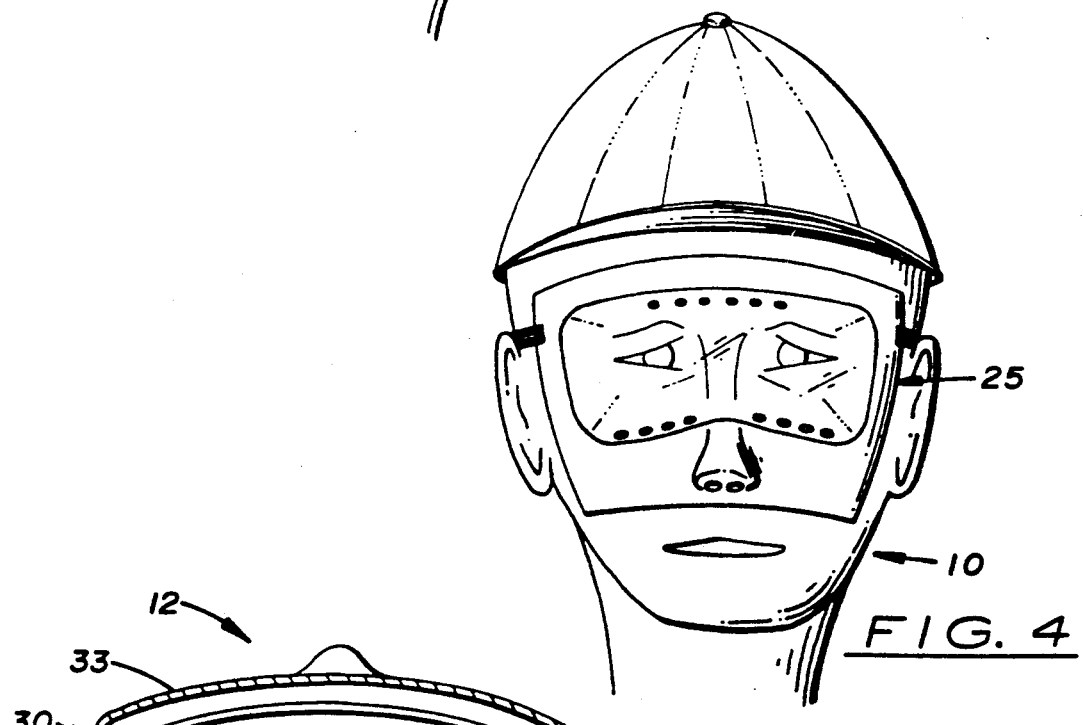
FIG. 4 is a plan view of an alternative embodiment of the face mask device having an alternative face mask structure.

Face mask structure 14 is made of lightweight, shatter-resistant material such as acrylic plastic or fiberglass material and may be manufactured in different shapes and styles. For example, FIG. 4 shows an alternative face mask structure 25 manufactured narrower and shorter than face mask structure 14 for a wearer who wants less protection and greater comfort.

Figure 3:
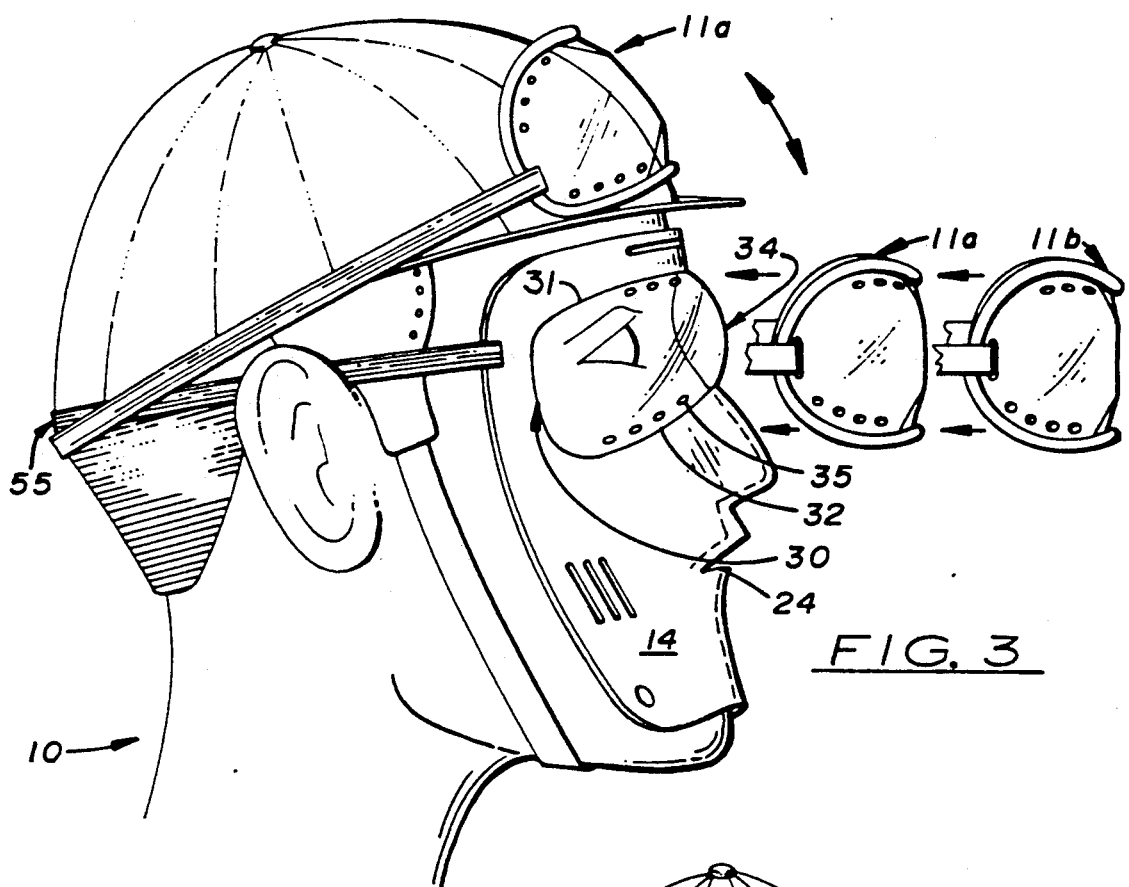
FIG. 3 is a sectional, side elevational view taken along lines 3—3 in FIG. 2.

The eye piece 30 is attached near the eye region of the face mask structure 14. As shown in FIGS. 2 and 3, in the preferred embodiment, the eye piece 30 extends substantially across the face mask structure 14 to provide wide-angled vision. The top edge 31 of the eye piece 30 extends horizontally across the forehead region slightly above the eyebrows while the bottom edge 32 extends horizontally across the mid-nose region of the face mask structure 14. In the preferred embodiment, eye piece 30 is a continuous piece made of shatter-resistent, distortion free, transparent material, such as acrylic plastic material. Eye piece 30 is attached to face mask structure 14 by conventional attachment methods, such as gluing or heat welding. Optional ventilation holes 35 may be manufactured near the top and bottom edges 31 and 32, respectively, to prevent fogging and moisture build up.

Figure 5:
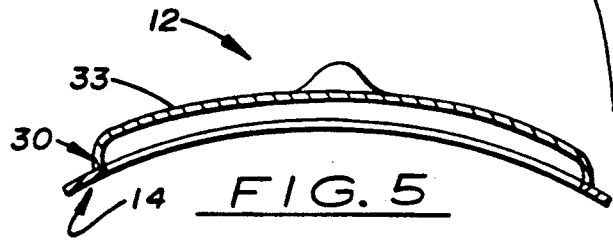
FIG. 5 is a sectional, top view of the face mask device taken along lines 5—5 in FIG. 2.

As shown in FIG. 1 and as mentioned above, an additional function of the eye piece 30 is to engage an outer goggle 11 placed over the face mask structure 14 during use. Conventional horse racing goggles 11 measure approximately 2 ½ inches (H)×7 inches (W) and, while worn, extend forward approximately ¾ inch from the eye surface. As shown in FIG. 3, the central region 34 of the eye piece 30 is round and protrudes forward from the face mask structure 14. In the preferred embodiment, central region 34 is complimentary in shape to the inside surface of the outer goggle 11 and extends approximately ¾ inch from the mask surface. This allows the inside surface of the outer goggle 11 to slidingly engage the central region 34 of the eye piece 30. As shown in FIG. 5, the outer surface 33 of the eye piece 30 is spherical in cross-section which enables eye piece 30 to engage the entire inside surface of the outer goggle 11. As shown in FIG. 3, the round, forward projecting surface of central region 34 enables eye piece 30 to slidingly engage a first pair of outer goggles 11(a) for quick and easy placement and removal with one hand. The central region 34 securely holds goggle 11(a) in place so that a second pair of outer goggles 11(b) may be stacked above the first pair of outer goggles 11(a).

Figure 6:
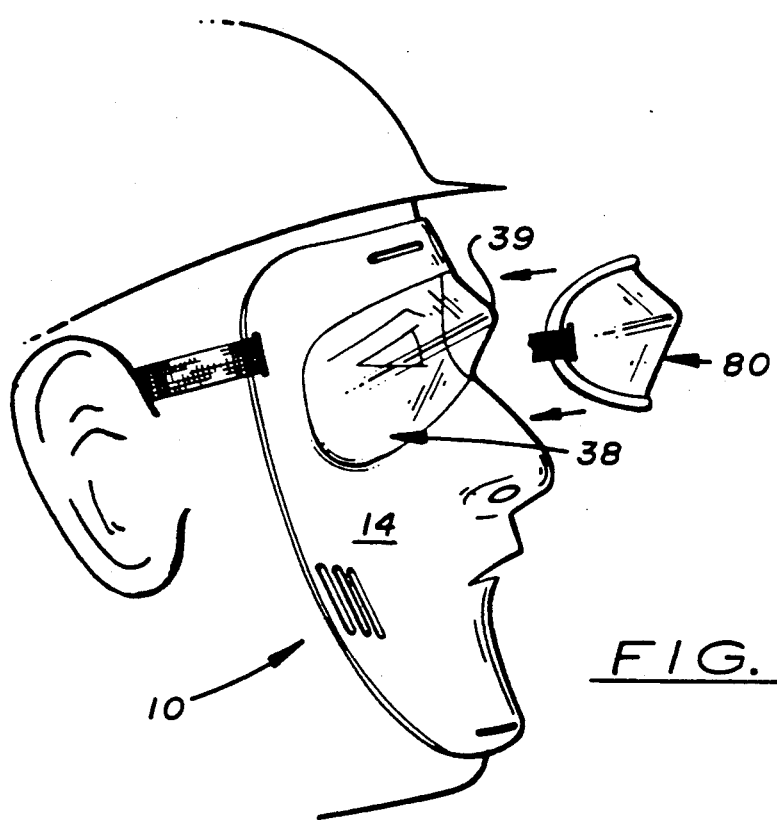
FIG. 6 is a sectional, side elevational view of an alternative embodiment of the face mask device having an eye protection means.

As seen in FIG. 6, the eye protecting means on device 12 may be modified. Eye piece 38 has a central region 39 which is angled or pointed forward from the face mask structure 14 which enables different goggle designs 80 to be slidingly engaged thereon.

Figure 7:
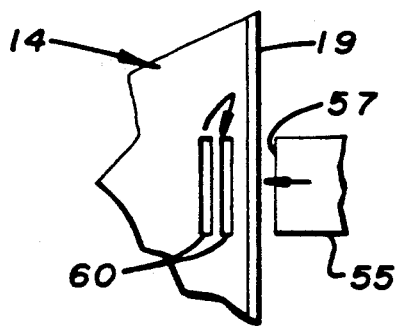
FIG. 7 is a partial side elevational view of the device showing the detachable end of the strap structure being attached to the opposite lateral edge of the face protecting means.
Figure 8:
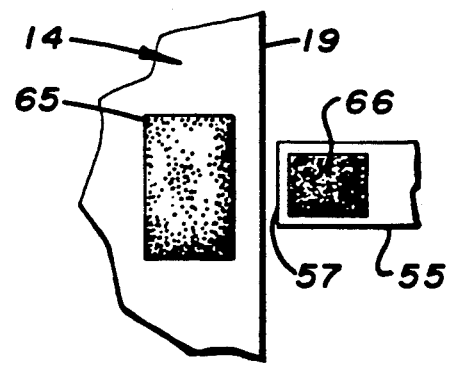
FIG. 8 is a partial, side elevational view of the device showing hook and loop connectors disposed between the opposite lateral edge of the face protection means and the detachable end of the strap structure.

As seen in FIGS. 1, 2, 3, and 6, the holding means comprises a strap structure 55 which holds the face mask device 12 on the face. In the preferred embodiment, the strap structure 55 is made of elastic nylon material which wraps around the wearer's 10 neck or head. Strap structure 55 has an attached end 56 and an opposite detachable end 57. The attached end 56 is connected to the first lateral edge 18 of the face mask structure 14. The actual site of connection can vary depending upon the type of goggle and helmet used and the wearer's preference. Generally, however, strap structure 55 is connected to the first lateral edge 18 so that the strap structure 55 fits comfortably above or over the top portion of the wearer's 10 ear. As shown in FIG. 7, two vertical slots 60 are manufactured near the second lateral edge 19 of the face mask structure 14. The detachable end 57 of the strap structure 55 is wrapped around the head or neck, extended through the two vertical slots 60, and adjusted in length, to securely hold the face mask structure 14 in place. In another embodiment shown in FIG. 8, hook and loop connectors 65 and 66, respectively, are disposed between second lateral edge 19 and near detachable end 57 to adjustably attach strap structure 55 to the face mask structure 14.

As shown in FIG. 1, during use the face mask device 12 is attached to the wearer's 10 face by aligning the face mask structure 14 on the face so that wide angled vision is obtained. Once properly positioned, the strap structure 55 is wrapped, adjusted in length, and attached to the opposite lateral edge 18 to secure device 12 around wearer's 10 head. The outer goggle 11 is then slidingly attached to the eye piece 30 using one hand.

The round, forward projecting central region 34 of the eye piece 30 protrudes forward towards the inside surface of outer goggles 11. When the activity is completed, face mask device 12 is removed from the wearer's 10 head by disconnecting detachable end 57 from the lateral edge 19 or by pulling the strap structure 55 over the head.

In addition to disclosing device 12 used for protecting the face and eyes of a wearer, a method of maintaining clear vision of a wearer using a goggle engaging face mask device, such as device 12, is also disclosed herein. The method comprises the following steps: (a) attaching and securing a goggle engaging face mask on the face of a wearer; (b) attaching and stacking a plurality of goggles over the eye protecting means on the goggle engaging face mask; (c) removing the most outer goggle from the stack of goggles when vision through the most outer goggle is impaired, thereby exposing a lower goggle which provides clear vision again for the wearer; (d) repeating step "c" until the last goggle is used or until the task is completed, and; (e) removing the goggle engaging face mask from the face of the wearer.

In compliance with the statute, the invention has been described in language more or less specific as to structural features. It should be understood, however, that the invention is not limited to the specific features shown since the means and construction shown comprise preferred forms of putting the invention into effect. The invention is, therefore, claimed in any of its forms or modifications within the legitimate and valid scope of the amended claims, appropriately interpreted in accordance with the doctrine of equivalents.

INDUSTRIAL APPLICABILITY

The device and method disclosed herein will find wide use by individuals who need both face and eye protection and clear vision while performing outdoor activities. This device is directly applicable in outdoor racing activities, such as horse or motorcycle racing, where vision through an outer goggle may be impaired during the race.

I claim:

1. A goggle engaging face mask device, comprising:
   a. an outer goggle;
   b. a face mask structure, said face mask structure having a first lateral edge and an opposite, second lateral edge;
   c. a transparent eye piece attached to said face mask structure and positioned in front of the eyes of a wearer of said device, said eye piece being curvilinear in cross-section and having a forward projecting central region which has a shape that is complimentary to the inside surface of said outer goggle thereby enabling said wearer to slidingly engage and align said outer goggle over said eye piece during use, and;
   d. a holding means for holding said face mask structure on the face of said wearer.

2. A device as recited in claim 1, wherein said face mask structure has a plurality of air ventilation slots located on its surface.

3. A device as recited in claim 1, wherein said face mask structure is made of lightweight, shatter-resistant material.

4. A device as recited in claim 3, wherein said face mask structure is made of acrylic plastic material.

5. A device as recited in claim 1, wherein said face mask structure is made of lightweight, flexible material.

6. A device as recited in claim 1, wherein said face mask structure has an upper edge that extends horizontally across the forehead and a lower edge that extends horizontally across the mouth or lower jaw of said wearer thereby substantially covering the entire the face of said wearer when worn.

7. A device as recited in claim 1, wherein said eye piece extends substantially across said face mask structure enabling said wearer to see, said eye piece having a top edge that extends horizontally across the forehead slightly above the eyebrows and a bottom edge that extends horizontally across the mid-nose region of said face mask structure.

8. A device as recited in claim 7, wherein said forward projecting central region of said eye piece is round.

9. A device as recited in claim 7, wherein said forward projecting central region of said eye piece is pointed.

10. A device as recited in claim 1, wherein said eye piece is made of acrylic plastic material.

11. A device as recited in claim 1, wherein said holding means is a strap structure capable of being wrapped around the head or neck of said wearer to hold said face mask structure on the face of said wearer, said strap structure being made of elastic material having an attached end and a detachable end, said attached end being connected to said first lateral edge by attachment means and said detachable end being extended through two slots located near said second lateral edge to adjustably connect said detachable end to said second lateral edge.

12. A device as recited in claim 1, wherein said holding means is a strap structure capable of being wrapped around the head or neck of said wearer to hold said face mask structure on the face of said wearer, said strap structure being made of elastic material having an attached end and a detachable end, said attached end being connected to said first lateral edge by attachment means, said device having hook and loop connectors disposed between said second lateral edge and said detachable end enabling said detachable end to be adjustably connected to said second lateral edge.

13. A device as recited in claim 1, wherein said outer goggle is a conventional horse racing goggle.

14. A goggle engaging face mask, comprising:
   a. an outer goggle;
   b. a face mask structure manufactured to conform and cover the entire face of a wearer, said face mask structure having a first and a second lateral edge;
   c. a transparent eye piece attached to said face mask structure so that when said face mask is worn said eye piece is positioned in front of the eyes of said wearer enabling said wearer to see clearly, said eye piece being curvilinear in cross-section and having a forward projecting central region, said forward projecting central region having a shape that is complimentary to the entire inside surface of said outer goggle thereby enabling said wearer to slidingly engage and align said outer goggle over said eye piece during use, said eye piece being made of shatter-resistant material, and;
   d. at least one strap structure attached to said face mask structure capable of holding said face mask structure on the face of said wearer, said strap structure being made of elastic material and capable of being wrapped around the head or neck of said wearer, said strap structure having an attached end connected to said first lateral edge of said face mask structure by first attachment means and a detachable end capable of being attached to said second lateral edge of said face mask structure by second attachment means.

15. A device as recited in claim 14, wherein said face mask structure is made of acrylic plastic material.

16. A device as recited in claim 14, wherein said outer goggle is a conventional horse racing goggle.

17. A device as recited in claim 14, wherein said second attachment means comprises hook and loop connectors disposed between said second lateral edge and said detachable end of said strap structure thereby enabling said second lateral edge and said detachable end of said strap structure to be adjustably attached.

18. A method of protecting the face and eyes and maintaining clear vision of a wearer while performing a task, comprising the following steps:

a. attaching and securing a goggle engaging face mask device over the face of said wearer, said goggle engaging face mask device having a transparent eye piece, said eye piece having a forward projecting central region which enables said wearer to see clearly and which enables an outer goggle to be slidingly engaged over said eye piece during use;

b. attaching and stacking a plurality of goggles over said eye piece;

c. removing the most outer goggle from the stack of said goggles when the vision through said most outer goggle is impaired thereby exposing a lower said goggle to provide clear vision again for said wearer;

d. repeating step "c" until the last said goggle is used or until said task is completed, and;

e. removing said device from said face of said wearer.

* * * * *